United States Patent [19]

Ferrari et al.

[11] Patent Number: 4,962,298

[45] Date of Patent: Oct. 9, 1990

[54] MACHINE FOR THERMALLY TREATING AND STERILIZING PRE-PACKAGED FOOD ARTICLES BY MEANS OF MICROWAVES

[75] Inventors: Claudio Ferrari; Oreste Caselli, both of Reggio Emilia, Italy

[73] Assignee: Barilla G.E.R. F.LII-Societa per Azoni, Parma, Italy

[21] Appl. No.: 381,359

[22] Filed: Jul. 18, 1989

[30] Foreign Application Priority Data

Jul. 18, 1988 [IT] Italy .............................. 21405 A/88

[51] Int. Cl.$^5$ .............................................. H05B 6/78
[52] U.S. Cl. ..................... 219/10.55 A; 219/10.55 F; 219/10.55 E; 426/243; 426/234; 99/DIG. 14
[58] Field of Search ................. 219/10.55 A, 10.55 F, 219/10.55 R, 10.55 E, 10.55 M; 426/234, 241, 243; 99/DIG. 14, 451

[56] References Cited

U.S. PATENT DOCUMENTS

| | | | |
|---|---|---|---|
| 2,704,802 | 3/1955 | Blass et al. | 219/10.55 F |
| 3,263,052 | 7/1966 | Jeppson et al. | 219/10.55 A |
| 3,427,171 | 2/1969 | Jeppson | 219/10.55 A |
| 3,851,133 | 11/1974 | Dygve et al. | 219/10.55 F |
| 4,160,145 | 7/1979 | Rueggeberg | 219/10.55 F |
| 4,210,793 | 7/1980 | Fournet-Fayas | 219/10.55 F |
| 4,624,854 | 11/1986 | Naumann et al. | 426/241 |
| 4,808,782 | 2/1989 | Nakagawa et al. | 219/10.55 A |
| 4,839,485 | 6/1989 | Koch et al. | 219/10.55 A |

*Primary Examiner*—Philip H. Leung
*Attorney, Agent, or Firm*—Sughrue, Mion, Zinn, Macpeak & Seas

[57] ABSTRACT

A machine for thermally treating and sterilizing pre-packaged food articles using microwaves, which is of a type comprising a treatment tunnel having inlet and outlet ports, a conveyor laid longitudinally of the tunnel interior between the ports to convey food article packages laid into parallel rows, at least one microwave generator having microwave radiators arranged to face the rows of packages, further comprises at least one microwave resonance chamber associated with at least one radiator as an extension thereof and extending at one of the rows, through a chamber wall facing the conveyor there being formed a plurality of slots. The machines enables selective heating of the rows of pre-packaged food articles to make the temperature inside the treatment tunnel uniform.

7 Claims, 2 Drawing Sheets

MACHINE FOR THERMALLY TREATING AND STERILIZING PRE-PACKAGED FOOD ARTICLES BY MEANS OF MICROWAVES

BACKGROUND OF THE INVENTION

This invention relates to a machine for thermally treating and sterilizing pre-packaged food articles by means of microwaves, being of a type which comprises a treatment tunnel provided with an inlet port and an outlet port, a conveyor extending longitudinally of the tunnel interior between said ports to convey packages of said food articles laid in parallel rows, at least one microwave generator within said tunnel, and microwave radiators arranged to face said rows.

Machine of this general type are currently widely employed in the industry to carry out thermal treatments accompanied by sterilization on pre-packaged food articles prepared on a commercial scale for subsequent distribution and retail sale, possibly in the frozen form.

The microwave treatment carried on such machines, while being in more than one way advantageous and generally more effective than traditional thermal treatment methods, has nevertheless the drawback specified herein below.

Where, for example, the articles are contained in trays orderly laid in parallel longitudinal rows on a pan-like carrier, lack of uniformity is encountered in the temperature, along a normal direction to the direction of advance of the articles on the conveyor belt. In other words, all the trays which occupy the same position in succession are subjected to the same thermal treatment, but trays in different rows have temperatures which differ from one another.

This brings about a serious problem in that an effective sterilization of the article is impaired which can only be achieved if a predetermined temperature can be held stable for a prearranged time period.

Furthermore, it cannot be postulated of obviating this drawback by an increase in the energy radiated in the treatment tunnel, to thus increase the average treatment temperature, because due to the very disuniformity in the temperatures reached some articles might undergo excessive heating and become burned locally.

SUMMARY OF THE INVENTION

The technical problem which underlies this invention is to provide a machine for thermally treating and sterilizing pre-packaged food articles by means of microwaves having such structural and performance characteristics as to afford a desired temperature profile through at least a section of the treatment tunnel.

This problem is solved by a machine as indicated being characterized in that it comprises at least one microwave resonance chamber associated with at least one radiator as an extension thereof and extending parallel to the conveyor at one of said rows, with a plurality of slots being formed in a chamber wall facing the conveyor.

The features and advantages of a machine according to the invention will become more clearly apparent from the following detailed description of an embodiment thereof, to be taken by way of illustration and not of limitation in conjunction with the accompanying drawings.

DETAILED DESCRIPTION OF THE INVENTION

Figure 1:
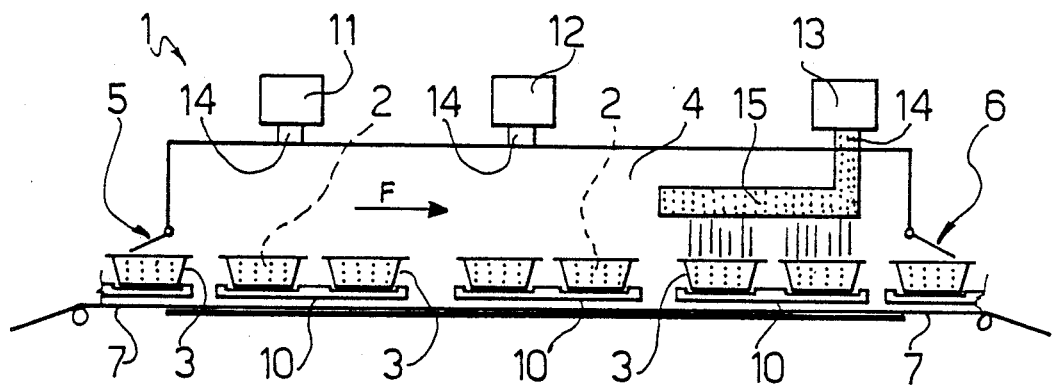
FIG. 1 is a longitudinal section view showing the machine of this invention in schematic form.
Figure 2:
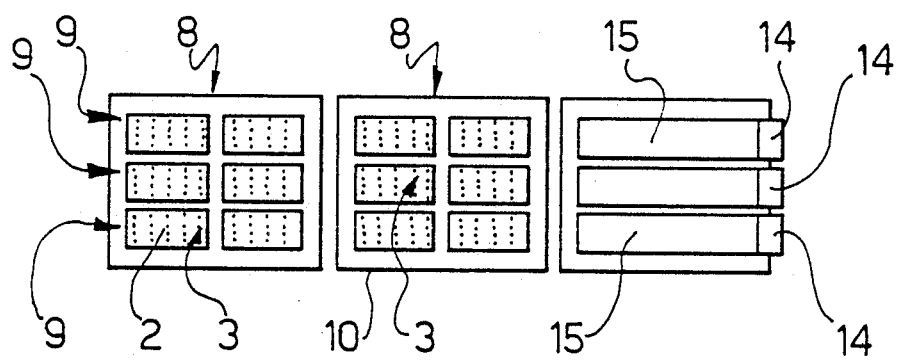
FIG. 2 is a horizontal section view showing schematically the machine of FIG. 1.

With reference to the drawing views, the numeral 1 generally and schematically designates a machine embodied in accordance with this invention. The machine 1 is particularly, but not exclusively, designed for the thermal treatment, accompanied by sterilization, of food articles 2 as preferably pre-packaged in trays 3.

The machine 1 comprises a treatment tunnel 4 having an inlet port 5 and an outlet port 6. Also provided is a belt conveyor 7 extended longitudinally through the tunnel 4, between the ports 5 and 6, and adapted to convey groups 8 of said trays 3 with the latter orderly laid in parallel rows 9 aligned in the direction F of advance on pan-like carriers 10.

The machine 1 also comprises three generators 11, 12 and 13 of electromagnetic microwaves which are set at substantially equal intervals inside the tunnel 4 and equipped with respective microwave radiators 14 facing the belt 7.

Advantageously, the third generator 13, which locates closest to the outlet port 6, includes a plurality of resonance chambers forming extensions of each radiator 14 and extending parallel to one another above the belt 7 and the rows 9 of trays 3, at each row.

The chambers 15 basically constitute guides for the electromagnetic wave; they have a box-like elongate shape of rectangular cross-section, and comprise side walls made of a material having a high electrical conductivity and low magnetic permeability, such as aluminum, thereby they are reflective of the electromagnetic energy delivered into the chamber.

Also provided are plural slots 16 formed through a side wall of the chamber 15.

Figure 3:
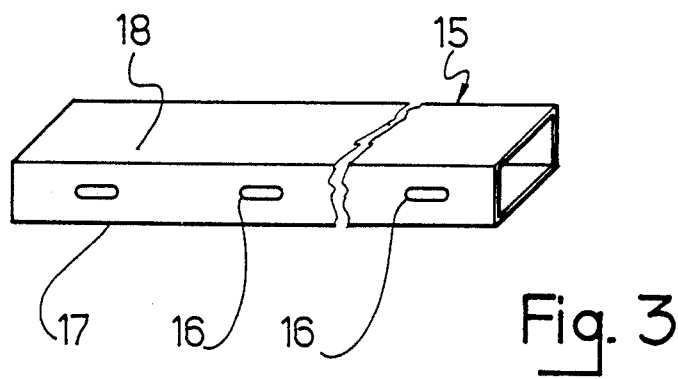
FIGS. 3 to 7 are respective detail views, in perspective, of the machine shown in FIG. 1.
Figure 4:
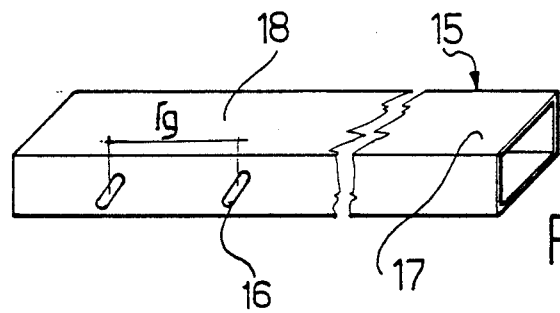
Figure 5:
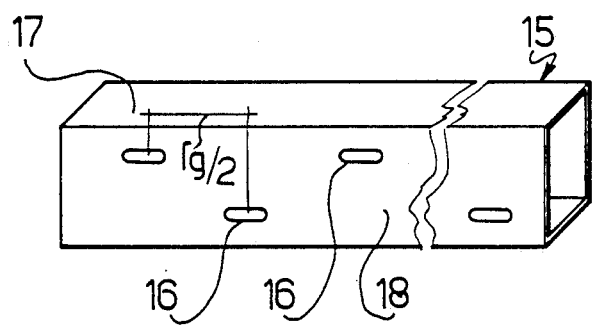
Figure 6:
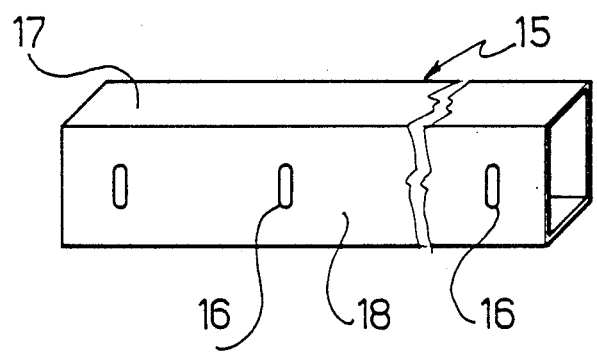
Figure 7:
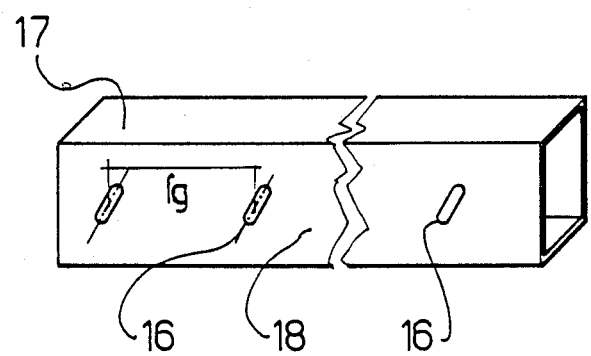

In FIGS. 3 and 4, there are shown the slots 16 as formed through a small-width one of the walls 7, whereas the remaining FIGS. 5, 6 and 7 show respective embodiments wherein such slots 16 are cut through a large-width wall 18 of the chamber 15.

Advantageously, throughout the several embodiments discussed by way of illustration and not of limitation with reference to said FIGS. 3 to 7, the slots 16 may be either aligned to the longitudinal axis of the wall accommodating them, or arranged parallel to one another at a predetermined inclination angle to that axis. In other embodiments, they may be either arranged to be normal to the axis or aligned into two parallel rows lying on opposite sides of the wall axis and set into alternate alignment.

The slots 16 are set equally apart by a distance equal to the wavelength $l_g$ of the electromagnetic radiation within the resonance chamber 15; in addition, the length of such slots 16 is equal to one half the wavelength $l$ of the microwaves in free space. The width of the slots 16 is negligible compared to their length and set to be 6 mm.

The chambers 15 extend parallel above, or beneath, the belt 7 with the slots 16 facing that belt and, hence, the rows 9 of the trays 3.

Contingent on requirements, chambers 15 would be installed having different arrangements of the slots 16, thereby the power of the microwaves radiating on the trays 3 can be modulated through such slots, thus enabling adjustment of the unbalanced temperatures normally present between rows 9.

The strength of the electromagnetic radiation delivered from the radiator 14 into the resonance chamber 15 is amplified by the resonant oscillations set up in the cavity of the chamber 15 (the phenomenon obeying the known "slot antenna" theory).

The frequency of the electromagnetic radiation normally employed for such applications is 2450 MHz, and corresponds to a wavelength l of 122 mm in free space. Inside the chamber 15, the wavelength lg of the radiation becomes instead 174 mm with a passage cross-section of $9 \times 4.7$ cm.

The value of the last-named parameter is used to adjust the distance separating the slots 16 formed through the side walls of the chamber 15. By offsetting, or setting at an angle, the slots 16, the power of the radiation issuing therefrom is also modulated to enable selective heating of the articles contained in the trays 3.

Thus, the machine of this invention affords control over the temperature distribution, both locally inside each tray and within the treatment tunnel 4, in particular for each row of the articles to be heated.

Each wave guide resonance chamber constitutes a radiator "spotted" over each article row and capable of supplying an appropriate amount energy to bring the article to the desired temperature, which can be stabilized for a predetermined time duration to carry out the sterilization step.

A major advantage afforded by the inventive machine is, therefore, that the temperature inside the treatment tunnel can be made uniform to compensate, in a simple and effective manner, conditions of unbalanced thermal treatment as usually undergone by the articles on conventional machines.

We claim:

1. A machine for thermally treating and sterilizing pre-packaged food articles by means of microwaves, comprising:
    an elongated treatment tunnel provided with an inlet port and an outlet port;
    a movable conveyor extending longitudinally within the tunnel between said ports to convey packages of food articles laid in parallel rows on said conveyor;
    a plurality of microwave generators disposed in spaced relation longitudinally along said conveyor,
    a plurality of microwave radiators connected to said generators and arranged to face said rows, respectively, and
    a plurality of elongated microwave resonance chambers connected to each respective microwave radiator connected to the generator closest to said outlet port and extending parallel to said conveyor above each respective row with each microwave resonance chamber having an elongated rectangular box-like configuration and having a plurality of slots formed in a chamber wall facing said conveyor.

2. A machine according to claim 1, characterized in that said slots are aligned to the axis of said wall.

3. A machine according to claim 1, characterized in that said slots extends parallel to one another at an angle to the axis of said wall.

4. A machine according to claim 1, characterized in that said slots are laid at equal distances apart normal to the axis of said wall.

5. A machine according to claim 1, characterized in that said slots are aligned parallel to the axis of said wall.

6. A machine according to claim 1, characterized in that said slots are separated by regular distances equal to the wavelength of the microwave present in said resonance chamber.

7. A machine according to claim 1, characterized in that the length of said slots is equal to one half the microwave wavelength in free space.

* * * * *